United States Patent [19]

Albert et al.

[11] Patent Number: 5,061,596
[45] Date of Patent: Oct. 29, 1991

[54] SILICON NAPHTHALOCYANINES AND THIN RADIATION SENSITIVE COATING FILMS CONTAINING SAME

[75] Inventors: Bernhard Albert, Maxdorf; Peter Neumann; Sibylle Brosius, both of Mannheim, all of Fed. Rep. of Germany

[73] Assignee: BASF Aktiengesellschaft, Ludwigshafen, Fed. Rep. of Germany

[21] Appl. No.: 321,377

[22] Filed: Mar. 10, 1989

[30] Foreign Application Priority Data

Mar. 31, 1988 [DE] Fed. Rep. of Germany ....... 3810956

[51] Int. Cl.$^5$ .................. G03C 1/72; C09B 47/00; C09B 47/04
[52] U.S. Cl. .................................. 430/270; 430/944; 430/945; 540/128
[58] Field of Search .................. 430/944, 945, 270; 540/128

[56] References Cited

U.S. PATENT DOCUMENTS

| | | | |
|---|---|---|---|
| 4,631,328 | 12/1986 | Ringsdorf et al. | 526/259 |
| 4,702,945 | 10/1987 | Etzbach et al. | 428/1 |
| 4,749,637 | 6/1988 | Hayashida et al. | 430/58 |

FOREIGN PATENT DOCUMENTS

| | | |
|---|---|---|
| 191215 | 7/1985 | European Pat. Off. . |
| 0191970 | 8/1986 | European Pat. Off. . |
| 0254553 | 1/1988 | European Pat. Off. . |

OTHER PUBLICATIONS

J. Amer. Chemistry for vol. 106, pp. 7404 to 7410, 1984.
J. Org. Chem. USSR (Engl. Translation) vol. 7, pp. 364 to 366, 1971.

Primary Examiner—Cynthia Hamilton
Attorney, Agent, or Firm—Oblon, Spivak, McClelland, Maier & Neustadt

[57] ABSTRACT

Thin radiation sensitive coating films contain silicon naphthalocyanines of the formula

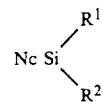

where
Nc is the radical of a naphthalocyanine system which may be substituted by $C_1$-$C_{10}$-alyl or $C_1$-$C_{10}$-alkoxy, and
$R^1$ and $R^2$ are indentical or different and each is independently of the other a radical of the formula

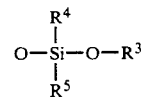

where $R^3$ is branched $C_6$-$C_{20}$-alkyl of the formula

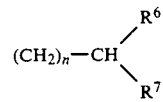

where n is from 1 to 5 and $R^6$ and $R^7$ independently of each other are $C_1$-$C_{16}$-alkyl, and $R^4$ and $R^5$ are independently of each other $C_1$-$C_{10}$-alkyl or the radical $OR^3$ where $R^3$ is as defined above, or the radical $R^1$ may also be $C_1$-$C_{10}$-alkyl.

3 Claims, No Drawings

SILICON NAPHTHALOCYANINES AND THIN RADIATION SENSITIVE COATING FILMS CONTAINING SAME

The present invention relates to a novel silicon naphthalocyanine where either or both of the ligands present on the central silicon atom contain a further silicon atom and to thin radiation sensitive coating films containing a base and a radiation sensitive layer which contains the novel compounds.

Recording materials which on exposure to radiation of high energy density, for example laser light, undergo a locally confined change of state are known. This thermally initiated change of state, for example evaporation, change of flow or fading, entails a change in the optical properties, for example the reflectance or absorption, due to a change in the absorption maximum or the absorbance, which can be utilized for information or data recording.

Suitable light sources for an optical recording system are for example semiconductor lasers which emit light in the near infrared. Of special interest are solid state injection lasers, in particular the AlGaAs laser, which operates in the wavelength range from about 650 to 900 nm. There is therefore particular interest in those recording materials which absorb radiation in the wavelength range from about 650 to 900 nm and can be made into thin, homogeneous layers.

J. Amer. Chem. Soc. 106 (1984), 7404–7410, and EP-A-191,215 disclose some silicon naphthalocyanines whose ligands on the central silicon atom each additionally contain a silicon atom. It has emerged, however, that the compounds described therein still show defects on use in optical storage systems.

It is an object of the present invention to provide novel radiation sensitive products which show good reflectance and high absorption in the wavelength range of the semiconductor lasers used. It is another object of the present invention to provide novel radiation sensitive coating films where the layers containing the novel products are homogeneous, show good adhesion to customary base materials and are stable over a long period.

We have found that these objects are achieved with novel silicon naphthalocyanines of the formula I

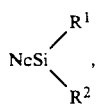
(I)

where
Nc is the radical of a naphthalocyanine system which may be unsubstituted or substituted by $C_1$–$C_{10}$-alkyl or $C_1$–$C_{10}$-alkoxy, and
$R^1$ and $R^2$ are identical or different and each is independently of the other a radical of the formula

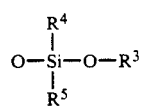

where $R^3$ is branched $C_6$–$C_{20}$-alkyl of the formula

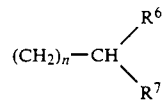

where n is from 1 to 5 and $R^6$ and $R^7$ are identical or different and each is independently of the other $C_1$–$C_{16}$-alkyl, and $R^4$ and $R^5$ are identical or different and each is independently of the other $C_1$–$C_{10}$-alkyl or the radical $OR^3$ where $R^3$ is as defined above, or the radical $R^1$ may also be $C_1$–$C_{10}$-alkyl.

The novel silicon naphthalocyanines are advantageously suitable for use as radiation sensitive components in thin radiation sensitive coating films.

All the alkyl groups appearing in the abovementioned radicals can be not only straight-chain but also branched, unless otherwise stated.

Examples of suitable substituents for the naphthalocyanine system are - apart from the radicals $R^1$, $R^4$, $R^5$, $R^6$ and $R^7$-methyl, ethyl, propyl, isopropyl, butyl, isobutyl, sec.-butyl, tert.-butyl, pentyl, isopentyl, neopentyl, tert.-pentyl, hexyl, 2-methylpentyl, heptyl, octyl, 2-ethylhexyl, isooctyl, nonyl, isononyl, decyl and isodecyl.

Further examples of suitable substituents for the naphthalocyanine system are methoxy, ethoxy, propoxy, isopropoxy, butoxy, isobutoxy, pentyloxy, hexyloxy, heptyloxy, octyloxy, 2-ethylhexyloxy, isooctyloxy, nonyloxy, isononyloxy, decyloxy and isodecyloxy.

Further examples of $R^6$ and $R^7$ are undecyl, dodecyl, tridecyl, 3,5,5,7-tetramethylnonyl, isotridecyl, tetradecyl, pentadecyl and hexadecyl. (The above designations isooctyl, isononyl, isodecyl and isotridecyl are trivial names which come from the oxo produced alcohols; cf. Ullmanns Enzyklopädie der technischen Chemie, 4th Edition, volume 7, pages 215 to 217, and volume 11, pages 435 and 436).

Important substituents for the naphthalocyanine system are for example $C_1$–$C_4$-alkyl, $C_5$–$C_{10}$-alkyl, $C_1$–$C_4$-alkoxy and $C_5$–$C_{10}$-alkoxy.

Important radicals $R^3$ are for example $C_6$–$C_{10}$-alkyl, $C_{10}$–$C_{15}$-alkyl and $C_{16}$–$C_{20}$-alkyl.

Important radicals $R^1$, $R^4$ and $R^5$ are for example $C_1$–$C_4$-alkyl and $C_5$–$C_{10}$-alkyl.

Important radicals $R^6$ and $R^7$ are for example $C_1$–$C_6$-alkyl, $C_7$–$C_{12}$-alkyl and $C_{13}$–$C_{16}$-alkyl.

Preference is given to those silicon naphthalocyanines of the formula I where Nc is the radical of an unsubstituted naphthalocyanine system.

The silicon naphthalocyanines according to the invention can be obtained in a conventional manner as described for example in J. Org. Chem. USSR (English translation) 7 (1971), 364–366, and J. Amer. Chem. Soc. 106 (1984), 7404–7410.

The starting materials used are for example the corresponding diiminoisoindolines of the formula II

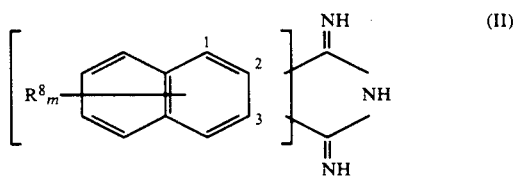
(II)

where $R^8$ is hydrogen, $C_1$–$C_{10}$-alkyl or $C_1$–$C_{10}$-alkoxy, m is 1 or 2, and the substituents capable of naphthalocyanine formation are always attached in the ortho position (positions 1 and 2 or 2 and 3).

These isoindolines of the formula II can be reacted with chlorosilanes of the formula III $$XSiCl_3 \quad (III),$$

where X is $C_1$–$C_{10}$-alkyl or chlorine, in an inert organic diluent in the presence of a base at from 170° to 250° C. to give chlorosilicon naphthalocyanines of the formula IV

where Nc and X are each as defined above.

Examples of suitable diluents are tetralin and nitrobenzene. Examples of suitable bases are tertiary amines such as tributylamine, quinoline, picolines and collidines.

The chlorosilicon naphthalocyanines IV can then be converted with concentrated sulfuric acid at from 5° to 50° C. into the corresponding hydroxy compounds of the formula V

where Y is hydroxyl or $C_1$–$C_{10}$-alkyl and Nc is as defined above.

By reacting the hydroxy compound V first with chlorosilanes of the formula VI $$X_2SiCl_2 \quad (VI),$$

where X is as defined above, in pyridine in the presence of sodium hydride at from 15° to 150° C. and then with alcohols of the formula VII $$R^3\text{—OH} \quad (VII),$$

where $R^3$ is as defined above, at from 30° to 120° C., it is finally possible to arrive at the silicon naphthalocyanines of the formula I according to the invention.

The novel silicon naphthalocyanines of the formula I show strong molar absorption in the near infrared. They form homogeneous, amorphous layers and/or are advantageously incorporable into dye-in-polymer layers.

The present invention further provides a thin radiation sensitive coating film containing a base and a radiation sensitive layer containing a silicon naphthalocyanine of the formula I.

Preference here is given to those radiation sensitive coating films which contain a silicon naphthalocyanine of the formula I where Nc is the radical of an unsubstituted naphthalocyanine system.

Further possible components of the thin coating films are polymers which are compatible with the compounds of the formula I. These polymers are in general referred to as binders.

Examples of suitable binders are polystyrenes, polyesters, polyacrylates, polymethacrylates, polycarbonates, polyamines, polyvinyl alcohols, polyvinyl chlorides, copolymers of vinyl chloride and vinyl acetate or polymers or copolymers as described in EP-A-90,282 or EP-A-171,045 that contain liquid crystalline side groups.

In addition, the films may contain further suitable additives, such as low molecular weight liquid crystalline compounds.

Preference is given to those films which consist only of silicon naphthalocyanines of the formula I and where the dyes are present in the amorphous state.

This term amorphous indicates that the coating film does not have any anisotropic regions which are greater than a fraction of the thermally altered regions, but that it is optically isotropic at about 30 nm and higher.

In general, the films are from 20 to 400 nm, preferably from 50 to 300 nm, in thickness.

Preferably, the dyes present in the coating films according to the invention absorb laser light, in particular laser light of relatively long wavelengths (650–900 nm).

Preference is given to those coating films which have been applied to a disklike base with or without a reflector layer and which make it possible for data to be written and reproduced by means of a semiconductor laser.

An optical storage system thus constructed can store high density information in the form of spirally or circularly concentric tracks, fine holes or depressions (about 1 μm in width) that are optically detectable from a change in the reflectivity compared with the surroundings. It shows good contrast.

Owing to the high light absorption of the dyes, the coating films according to the invention are very sensitive to the light from the semiconductor laser.

The structure of the recording media is known per se.

Suitable bases are for example glass plates or disks or plastics plates or disks, in particular plates or disks made of polymethyl methacrylate, polystyrene, polystyrene copolymers, polyvinyl chloride, polymethylpentene or polycarbonate, with or without tracking grooves.

Specifically, the base may take the form of a tape, a square or rectangular plate or a round disk, preference being given to the disks 10 or 13 cm in diameter customary and known for laser-optical recording materials.

In addition, the recording materials may have further layers, such as protective layers, adhesion-promoting layers or electrode layers.

Aside from the base there may also be present a reflective layer, so that the incident light passing through the colored layer is, if it is not absorbed, reflected at the reflector layer and passes once more through the colored layer.

Irradiation preferably takes place through a transparent substrate. A possible sequence of layers is then: substrate/absorbent layer/optional reflector.

The base or the light-reflecting layer must have an optically smooth, flat surface constituted in such a way that the absorbing layer is firmly adherent thereon. To improve the surface quality and adhesion phenomena, the base and/or the reflector may be coated with a planarizing layer of a thermosetting or thermoplastic material.

If the radiation sensitive layer does not have sufficient mechanical stability, it can be coated with a transparent protective layer. Suitable for this purpose are a number of polymers which can be applied in solution by spin-coating, knife coating or dipping or by vacuum vapor deposition, chiefly for fluorinated polymers, to form a protective layer.

If the data memory is constructed from two identical or different recording media in the form of a sandwich, a protective layer becomes dispensable. In addition to greater mechanical and rotation-dynamical stability, the sandwich construction offers the advantage of twice the storage capacity.

However, the protective and/or intermediate layers can also be dispensed with if the optical recording medium is of sufficient quality.

The thin coating films according to the invention, which contain the novel silicon naphthalocyanines, absorb strongly at the semiconductor laser wavelength of from about 650 to about 900 nm. The silicon naphthalocyanines may be applied in such a way as to produce smooth absorption layers of optical quality into which the information to be stored can be written with a high signal-to-noise ratio.

The absorption materials are preferably applied by spincoating with dissolved or dispersed dye in the presence or absence of binders. Other possible layer formation methods are knifecoating and dipping. Metallic reflection layers, for example, are preferably applied by vacuum vapor deposition or by mounting suitable metal foils on the base.

To apply the absorption layers from solution, a solution or, as the case may be, a dispersion of the silicon naphthalocyanine or a mixture of this compound and the binder is prepared in a suitable solvent, such as cyclohexane, methylcyclohexane, methylene chloride, chloroform, carbon tetrachloride, bromoform, 1,1,1-trichloroethane, 1,1,2-trichloroethane, acetone, methyl ethyl ketone, cyclohexanone, toluene, acetonitrile, ethyl acetate, methanol, ethanol or mixtures thereof, and an assistant may be added.

This dye preparation is then applied by knife coating or dipping but preferably by spincoating to a previously cleaned and/or pretreated substrate (subbing layer) and the layer is dried or hardened in the air. The film can also be dried or hardened at elevated temperature under reduced pressure or, where appropriate, by radiation.

As stated above, preference is given to those radiation sensitive coating films which consist only of one layer, in particular to those where this layer is applied by spincoating.

Depending on the system configuration, first the radiation sensitive layer is applied and then the reflector, or vice versa. The application of intermediate or protective layers or of a reflecting layer may, as stated above, also be dispensed with in certain circumstances.

A monolayer system without reflector is preferred.

The radiation sensitive coating films according to the invention can be written with analogue or digital data by means of a write laser beam which, as is common knowledge, uses an analogue modulated continuous wave laser if analogue data are to be written and a pulse code modulated laser if digital data are to be written.

In general, suitable lasers give a beam output of 1 to 20 mW at the writing wavelength. The focus diameter of the write laser beam is in general from 300 to 2000 nm. Customarily, the pulse duration for irradiation with a pulse code modulated laser is from 10 to 1000 ns. Advantageously, the write laser beam comprises light of a wavelength which is readily absorbed by the recording layer in question. Wavelengths of from 400 to 1000 nm are advantageous.

During writing, the laser beam is guided across the recording material in a relative motion while being perpendicularly focused on the recording layer. At the point of incidence the recording layer is locally heated, and thermally altered areas are formed, for example in the shape of holes, craters or spots. If data are written with pulse code modulated lasers these areas essentially have a round or oval shape from 100 to 2000 nm in diameter. If written with an analogue modulated continuous wave laser they may have any desired shapes.

The coating films according to the invention are highly suitable for laser-optical data recording.

The writing of the data into the recording layer can take place from the base remote side of the layer or through the optically clear base. The latter is of particular advantage.

The written data are read by means of a read laser beam. The beam power of the read laser at the read wavelength is below the power threshold at which writing becomes possible. In general, the beam power is from 0.1 to 1.5 mW. It is advantageous to use laser light of a wavelength which is strongly reflected by the recording layer. A wavelength of 400 to 1000 nm, in particular from 630 to 900 nm, is advantageous.

In reading, too, the read laser beam is guided across the recording material in a relative motion while being perpendicularly focused on the recording layer.

If, in scanning across the recording layer, the read laser beam comes across a thermally altered area, for example a spot, the properties of the light transmitted or reflected by the recording material change, which can be detected by means of suitable detectors.

This reading of the data in the recording layer may take place from the base remote side of the layer or through the optically clear, transparent base, the latter being of advantage. It is particularly advantageous here to detect the reflected light.

It is also of particular advantage to use for this purpose write and read lasers which emit in the infrared wavelength range from 650 to 900 nm. It is also of advantage here if the writing wavelength is identical to the read wavelength or differs therefrom only by a small amount. Light of these wavelengths is supplied by customary and known semiconductor lasers.

The coating films according to the invention have numerous particular advantages. For instance, their unwritten recording layer is particularly stable, so that even following prolonged storage at comparatively high temperatures and humidities it is still highly suitable for laser-optical data recording. The same is true of the written recording layer; here there is no information loss even on very long storage. It is therefore also possible to use write lasers of comparatively low beam power. Moreover, the written recording materials have a particularly high optical contrast between written and unwritten areas which exceeds the optical contrast of written phthalocyanine layers of the prior art. Furthermore, the novel recording materials make it possible to obtain a bit density of distinctly above $10^7$ bits/cm$^2$, and even then the data can be read immediately following the writing thereof.

The silicon phthalocyanines of the formula I according to the invention have further very good application properties and therefore can also be used for other purposes. In particular, they can be used for manufacturing IR protection layers, IR absorbent films, eyeshade coatings, coatings for automotive windshields, IR inks, printing inks for IR readable bar codes, liquid crystal displays or IR security systems.

IR readable bar codes are for example the bar codes applied to packaging to provide accurate identification of the goods inside.

Liquid crystal displays are the known arrangements which contain layers of liquid crystalline substances. These layers, on being subjected to an applied electrical voltage, undergo a local change in their optical properties, as a result of which for example numbers, letters or images can be visibly displayed.

IR security systems are arrangements which consist essentially of a laser light source and a suitable detector situated at a distance therefrom. The laser beam emitted by the laser light source passes to the detector, forming a light barrier. If this barrier is broken, the detector sends out an alarm.

Electrophotographic recording materials contain essentially layers which have a high electrical resistance in the dark but become conductive on exposure to light. If such layers are electrostatically charged at the surface in the dark and then subjected to imagewise exposure, the electrostatic charge is conducted away in the exposed areas, leaving an electrostatic image which can be made visible by means of toners.

The Examples below will further illustrate the invention.

A) Synthesis

EXAMPLE 1 a) Synthesis of

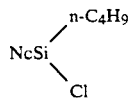

(Unless otherwise stated, the radical Nc in the examples always denotes the unsubstituted radical of the naphthalocyanine system).

20 g of n-butyl-trichlorosilane and 11 g of 1,3-diiminobenzo[f]isoindoline were heated in 150 ml of quinoline at 195° C. for 3 hours. After cooling down, 250 ml of methanol were added, the suspension was filtered with suction, and the filter residue was washed with methanol.

b) Synthesis of

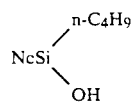

The compound obtained under a) was stirred at room temperature with concentrated sulfuric acid for 20 hours. The reaction mixture was then discharged on to ice-water, the mixture was filtered with suction, and the filter residue was washed with water and methanol.

c) Synthesis of

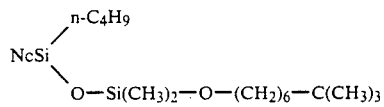

5 g of the compound described under b) were added to a mixture of 150 ml of pyridine, 50 ml of toluene and 10 ml of tributylamine. 0.5 g of sodium hydride was then added and stirred in at 80° C. for 3 hours. After cooling down, 20 ml of dimethyldichlorosilane [$(CH_3)_2SiCl_2$] were added, the mixture was stirred overnight at room temperature, and about 100 ml of the reaction mixture were then distilled off.

7 ml of 7,7-dimethyloctan-1-ol were added, the mixture was refluxed for 6 hours, substantially all the volatiles were then distilled off under the same conditions, and the mixture was cooled down and admixed with about 200 ml of methanol.

The target product was filtered with suction and washed with methanol.

The same method was used to obtain the compounds of the formula

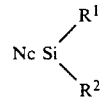

listed in Table 1 below, which also shows the silane and alcohol used in stage c).

To characterize these compounds, Table 2 presents their Rf values.

TABLE 1

| Example No. | $R^1 = R^2$ | Silane | Alcohol |
| --- | --- | --- | --- |
| 2 | $O-Si(CH_3)_2-O-n-C_8H_{17}$ | $(CH_3)_2SiCl_2$ | $n-C_8H_{17}OH$ |
| 3 | $O-Si(CH_3)_2-O-(CH_2)_2-OCH_3$ | $(CH_3)_2SiCl_2$ | $CH_3O(CH_2)_2OH$ |
| 4 | $O-Si(CH_3)_2-O-(CH_2)_2-O-(CH_2)_2-O-n-C_4H_9$ | $(CH_3)_2SiCl_2$ | $n-C_4H_9O(CH_2)_2O(CH_2)_2OH$ |
| 5 | $O-Si(CH_3)_2-O-(CH_2)_6-OH$ | $(CH_3)_2SiCl_2$ | $HO(CH_2)_6OH$ |
| 6 | $O-Si(CH_3)_2-O-CH(n-C_8H_{17})_2$ | $(CH_3)_2SiCl_2$ | $(n-C_8H_{17})_2CHOH$ |
| 7 | $O-Si(CH_3)_2-O-n-C_{18}H_{37}$ | $(CH_3)_2SiCl_2$ | $n-C_{18}H_{37}OH$ |
| 8 | $O-Si(CH_3)_2-O-n-C_{12}H_{25}$ | $(CH_3)_2SiCl_2$ | $n-C_{12}H_{25}OH$ |
| 9 | $O-Si(CH_3)_2-O-(CH_2)_6-C(CH_3)_3$ | $(CH_3)_2SiCl_2$ | $(CH_3)_3C(CH_2)_6OH$ |
| 10 | $O-Si(O-n-C_8H_{17})_3$ | $SiCl_4$ | $n-C_8H_{17}OH$ |
| 11 | $O-Si(O-n-C_{12}H_{25})_3$ | $SiCl_4$ | $n-C_{12}H_{25}OH$ |
| 12 | $O-Si(O-n-C_{18}H_{37})_3$ | $SiCl_4$ | $n-C_{18}H_{37}OH$ |
| 13 | $O-Si[O-(CH_2)_6-C(CH_3)_3]$ | $SiCl_4$ | $(CH_3)_3C(CH_2)_6OH$ |
| 14 | $O-Si(n-C_4H_9)(O-CH_2-\underset{\underset{C_2H_5}{\mid}}{CH}-C_4H_9)_2$ | $Cl_3Si-n-C_4H_9$ | $\underset{C_2H_5}{\overset{C_4H_9}{\diagdown}}CHCH_2OH$ |

TABLE 1-continued

| Example No. | $R^1 = R^2$ | Silane | Alcohol |
|---|---|---|---|
| 15 | O—Si(—CH$_2$—CH$_2$—CH(CH$_3$)$_2$)(O—CH$_2$—CH(C$_2$H$_5$)—C$_4$H$_9$) | Cl$_3$Si—(CH$_2$)$_2$—CH(CH$_3$)$_2$ | C$_4$H$_9$(C$_2$H$_5$)CHCH$_2$OH |
| 16 | O—Si(CH$_3$)$_2$—O—(CH$_2$)$_4$—CH(CH$_3$)$_2$ | (CH$_3$)$_2$SiCl$_2$ | (CH$_3$)$_2$CH(CH$_2$)$_4$OH |
| 17 | O—Si(CH$_3$)$_2$—O—(CH$_2$)$_3$—CH(C$_2$H$_5$)—C$_4$H$_9$ | (CH$_3$)$_2$SiCl$_2$ | C$_4$H$_9$(C$_2$H$_5$)CH(CH$_2$)$_3$OH |
| 18 | O—Si(CH$_3$)$_2$—O—CH$_2$—CH(C$_2$H$_5$)—C$_4$H$_9$ | (CH$_3$)$_2$SiCl$_2$ | C$_4$H$_9$(C$_2$H$_5$)CHCH$_2$OH |
| 19 | O—Si(CH$_3$)(n-C$_6$H$_{13}$)—O—CH$_2$—CH(C$_2$H$_5$)—C$_4$H$_9$ | Cl$_2$Si(CH$_3$)(n-C$_6$H$_{13}$) | C$_4$H$_9$(C$_2$H$_5$)CHCH$_2$OH |
| 20 | O—Si(CH$_3$)(n-C$_{12}$H$_{25}$)—O—CH$_2$—CH(C$_2$H$_5$)—C$_4$H$_9$ | Cl$_2$—Si(CH$_3$)(n-C$_{12}$H$_{25}$) | C$_4$H$_9$(C$_2$H$_5$)CHCH$_2$OH |

TABLE 2

| Example No. | Rf values Mobile phase: A | B | C |
|---|---|---|---|
| 1 |  | 0.42 | 0.89 |
| 2 | 0.55 | 0.43 | 0.84 |
| 3 |  | 0.10 |  |
| 4 |  | 0.66 |  |
| 5 |  | 0.66 | 0.84 |
| 6 |  | 0.90 |  |
| 7 | 0.57 | 0.83 | 0.87 |
| 8 |  | 0.53 |  |
| 9 | 0.88 | 0.89 | 0.94 |
| 10 |  | 0.08 |  |
| 11 |  | 0.15 | 0.98 |
| 12 |  | 0.87 | 0.98 |
| 13 |  | 0.98 | 0.96 |
| 14 |  | 0.25 | 0.97 |
| 15 |  | 0.48 | 0.97 |
| 16 | 0.62 | 0.65 | 0.94 |
| 17 |  | 0.91 | 0.96 |
| 18 | 0.67 | 0.72 | 0.95 |
| 19 |  | 0.44 |  |
| 20 |  | 0.75 |  |

The Rf values above were measured on silica gel plates from Macherey und Nagel (polygram 0.2 mm, N-HR UV 254).

The mobile phases used were
A) toluene
B) 9:1 v/v toluene/methylene chloride
C) 9:1 v/v toluene/acetone Manufacturing method for a coating film 1 g of compound of Example 1c) was stirred in 20 ml of toluene at room temperature overnight and then forced under superatmospheric pressure through a P4 sinter. The resulting solution was then applied by means of a syringe to a rotating disk of polymethyl methacrylate (diameter 12 cm), the disk being initially spun at 2000 rpm for 25 seconds and then at 5000 rpm for 35 seconds for drying. The layer obtained was homogeneous, pinhole-free and highly reflective.

B) Use

The recording material manufactured as described above was written and read using a customary and known measuring drive comprising a) a pulse code modulated write laser emitting light of wavelength 836 nm with a maximum power output of 10 mW and b) a read laser continuously emitting light of wavelength 780 nm with a power of 0.4 to 1 mW.

The measuring drive also included optical components by means of which the parallel laser beams of lasers (a) and (b) were made colinear for focusing with a common lens (NA=0.5) through the disks on the recording layers. As a result the points of incidence of the two laser beams were only about 10 μm apart, so that, as a consequence of the rotation of the disk, a written spot passed only a few μs after being written through the focus of the read laser (b) for detection.

To detect the spots, the light reflected by the recording layer through the disks was collected in a conventional manner.

The recording material was written at a tracking speed of 4 ms$^{-1}$ by means of the write laser (a) with continuous pulse waves (1 MHz square wave; duration of individual pulse: 500 ns), while the writing power was varied between 1 and 10 mW. Immediately thereafter, i.e. a few μs after being recorded, the spots obtained were read. The amplitude of the pulses of the reflected read laser light caused by the spots was measured and recorded as a function of the writing power with which the spots in question had been originally produced. In this way the minimum writing power for obtaining satisfactory signals—the basic prerequisite for data recording—under the above mentioned conditions was determined. It was possible to obtain satisfactory signals with a writing power level of as little as 2.5 mW, which evidenced the high sensitivity of the recording material according to the invention.

The recording material was stored at 60° C. and a relative humidity of 90% for ten weeks. No adverse changes were found; on the contrary, the recorded data were still as flawlessly readable as before.

We claim:

1. A silicon naphthalocyanine of the formula I

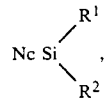

where

Nc is the radical of a naphthalocyanine system which is unsubstituted or substituted by $C_1$-$C_{10}$-alkyl or $C_1$-$C_{10}$-alkoxy, and $R^1$ and $R^2$ are indentical or different and each is independently of the other a radical of the formula

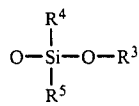

where $R^3$ is branched $C_6$-$C_{20}$-alkyl of the formula

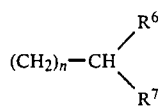

where n is from 1 to 5 and $R^6$ and $R^7$ are identical or different and each is independently of the other $C_1$-$C_{16}$-alkyl, and $R^4$ and $R^5$ are identical or different and each is independently of the other $C_1$-$C_{10}$-alkyl or the radical $OR^3$ where $R^3$ is as defined above, or the radical $R^1$ is also $C_1$-$C_{10}$-alkyl.

2. The silicon naphthalocyanine of the formula I as claimed in claim 1, wherein Nc is the radical of an unsubstituted naphthalocyanine system.

3. A thin radiation sensitive coating film containing a base and a radiation sensitive layer containing a silicon naphthalocyanine of the formula I

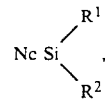

where

Nc is the radical of a naphthalocyanine system which is substituted by $C_1$-$C_{10}$-alkyl or $C_1$-$C_{10}$-alkoxy, and $R^1$ and $R^2$ are identical or different and each is independently of the other a radical of the formula

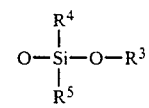

where $R^3$ is branched $C_6$-$C_{20}$-alkyl of the formula

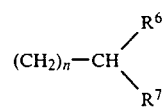

where n is from 1 to 5 and $R^6$ and $R^7$ are identical or different and each is independently of the other $C_1$-$C_{16}$-alkyl, and $R^4$ and $R^5$ are identical or different and each is independently of the other $C_1$-$C_{10}$-alkyl or the radical $OR^3$ where $R^3$ is as defined above, or the radical $R^1$ is also $C_1$-$C_{10}$-alkyl.

* * * * *